(12) United States Patent
Rycroft et al.

(10) Patent No.: US 10,377,536 B2
(45) Date of Patent: Aug. 13, 2019

(54) RADIATION CROSSLINKED POLYETHYLENE HINGE

(71) Applicant: NOVA Chemicals (International) S.A., Fribourg (CH)

(72) Inventors: Jason Rycroft, Calgary (CA); Gilbert Arnould, Calgary (CA); Matthew Botros, Calgary (CA); William McGrory, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 289 days.

(21) Appl. No.: 15/123,386

(22) PCT Filed: Jan. 29, 2015

(86) PCT No.: PCT/IB2015/050664
§ 371 (c)(1),
(2) Date: Sep. 2, 2016

(87) PCT Pub. No.: WO2015/132680
PCT Pub. Date: Sep. 11, 2015

(65) Prior Publication Data
US 2017/0107365 A1 Apr. 20, 2017

(30) Foreign Application Priority Data
Mar. 6, 2014 (CA) .................... 2844886

(51) Int. Cl.
*B65D 47/08* (2006.01)
*B32B 1/02* (2006.01)
(Continued)

(52) U.S. Cl.
CPC .............. *B65D 47/08* (2013.01); *B32B 1/02* (2013.01); *B65D 47/065* (2013.01);
(Continued)

(58) Field of Classification Search
CPC .... B65D 41/02; B65D 41/04; B65D 41/0407; B65D 41/0435; B65D 41/045;
(Continued)

(56) References Cited

U.S. PATENT DOCUMENTS

| 4,047,495 A | 9/1977 | O'Brian |
| 4,638,916 A | 1/1987 | Beck et al. |

(Continued)

FOREIGN PATENT DOCUMENTS

WO 2010/101915 A2 9/2010

OTHER PUBLICATIONS

ASTM D1238-13; Standard Test Method for Melt Flow Rates of Thermoplastics by Extrusion Plastometer; Copyright ASTM International; Current edition approved Aug. 1, 2013. Published Aug. 2013. Originally approved in 1965. Last previous edition approved in 2010 as D1238-10. pp. 1-16.

(Continued)

*Primary Examiner* — Walter Aughenbaugh
(74) *Attorney, Agent, or Firm* — Julie L. Henirich

(57) ABSTRACT

Polyethylene living hinges used in "snap top" lids for condiments and the like may be electron bean irradiated to partially crosslink the polyethylene to produce a hinge having an improvement in the number of opening and closing cycles until failure of not less than 30%. The irradiated lids may be used in place of polypropylene lids for condiment containers.

22 Claims, 4 Drawing Sheets

(51) Int. Cl.
    *B65D 51/04*  (2006.01)
    *B65D 83/20*  (2006.01)
    *B65D 47/06*  (2006.01)
    *C08L 23/08*  (2006.01)
    *G01M 5/00*   (2006.01)
    *G01N 3/36*   (2006.01)
    *C08J 3/24*   (2006.01)
    *C08J 7/12*   (2006.01)

(52) U.S. Cl.
    CPC ..... *B65D 47/0809* (2013.01); *B65D 47/0857* (2013.01); *B65D 51/04* (2013.01); *B65D 83/206* (2013.01); *C08J 3/24* (2013.01); *C08J 7/123* (2013.01); *C08L 23/0815* (2013.01); *G01M 5/0033* (2013.01); *G01M 5/0058* (2013.01); *G01N 3/36* (2013.01); *C08J 2323/08* (2013.01); *C08J 2423/08* (2013.01); *C08L 2205/025* (2013.01); *C08L 2312/06* (2013.01); *G01N 2203/0005* (2013.01); *G01N 2203/0023* (2013.01); *G01N 2203/0044* (2013.01); *G01N 2203/0282* (2013.01); *G01N 2203/0298* (2013.01); *G01N 2203/0464* (2013.01)

(58) Field of Classification Search
    CPC ............ B65D 41/0457; B65D 41/0464; B65D 41/0471; B65D 41/0478; B65D 41/0492; B65D 41/34; B65D 41/3423; B65D 41/3428; B65D 41/3447; B65D 47/065; B65D 47/08; B65D 47/0857; B65D 51/04; B65D 83/206; B32B 1/02; B32B 1/08
    See application file for complete search history.

(56)           References Cited

U.S. PATENT DOCUMENTS

| 5,148,912 | A   |         | 9/1992 | Nozawa                    |
|-----------|-----|---------|--------|---------------------------|
| 6,041,477 | A   |         | 3/2000 | Rentsch et al.            |
| 6,766,926 | B1  |         | 7/2004 | Elchert                   |
| 8,192,813 | B2  |         | 6/2012 | Runyan et al.             |
| D783,400  | S   | *       | 4/2017 | Bois .............. D9/449 |
| 2004/0118846 | A1 |       | 6/2004 | Merolla                   |
| 2006/0199911 | A1 | *     | 9/2006 | Markovich ......... C08L 23/0815 525/192 |
| 2010/0224646 | A1 |       | 9/2010 | Incorvia et al.           |

OTHER PUBLICATIONS

ASTM D5227-13; Standard Test Method for Measurement of Hexane Extractable Content of Polyolefins; Current edition approved Jun. 1, 2013. Published Jul. 2013. Originally approved in 1992. Last previous edition approved in 2008 as D5227-01 (2008). pp. 1-4.

* cited by examiner

RADIATION CROSSLINKED POLYETHYLENE HINGE

TECHNICAL FIELD

The present invention relates to electron beam cross linked polyethylene hinges for lids for dispensing containers such as condiments, spices, soaps, shampoos, oils and pills. Such hinges need to have a life cycle of at least about 300 openings and closing before failure (e.g. the hinge breaks). In some embodiments the lid snaps shut when gently pushed towards the closed position and stay open when pushed towards the fully opened position. These lids contain a hinge about which the cap or lid pivot to open and close. These lids are sometimes referred to as snap top lids. Sometimes the hinge element is referred to as a "living hinge".

BACKGROUND ART

There is extensive art in this field.

U.S. Pat. No. 4,047,495 issued Sep. 13, 1997 to O'Brian Sep. 13, 1997, assigned to Polytop Corporation teaches a "snap top" child proof lid for a container. The patent teaches the living hinge is preferably injection molded from polypropylene because of the well-known living hinge properties of polypropylene. Other olefin polymers can be used but are not preferred (Col. 4 lines 41-50). The patent does not teach or suggest that the other polyolefins could be modified by radiation crosslinking to provide improved properties.

U.S. Pat. No. 4,638,916 issued Jan. 27, 1987 to Beck et al. assigned to Owens-Illinois, Inc., teaches a snap type hinge cap. The structural elements of the lid are disclosed but there is no disclosure of what material the lid may be made from. One of ordinary skill in the art would likely select polypropylene as the preferred material. Further there is no suggestion to use radiation crosslinking to improve the properties of the hinge.

U.S. Pat. No. 5,148,912 issued Sep. 22, 1992 to Nozawa et al., assigned to Yoshino Kogyosho Co., Ltd., teaches a slightly different snap top lid in which there are two separate hinges or straps. Again there is no disclosure of what material the lid may be made from. One of ordinary skill in the art would likely select polypropylene as the preferred material. Further there is no suggestion to use radiation crosslinking to improve the properties of the hinge.

U.S. Pat. No. 6,041,477 issued Mar. 28, 2000 to Rentsch et al., also teaches the structural elements of a snap top lid which differ from the prior art. While the patent contains a warning about residual stress in snap top lids having adverse effects on injection moulding plastic material, (Col. 3 lines 28 to 35), nowhere in the specification is there a disclosure of suitable materials from which to make the hinge. Further there is no suggestion to use radiation crosslinking to improve the properties of the hinge.

U.S. Pat. No. 6,766,926 issued Jul. 27, 2004 to Elchert assigned to Owens-Illinois Closure Inc., teaches the type of closure most commonly seen to-day. The structural elements of the cap are clearly disclosed. However, again the material form which the cap may be made is not discussed. Further there is no suggestion to use radiation crosslinking to improve the properties of the hinge.

Crosslinked polyethylene (PEX) is well known. Some applications it is used in include pipe and wire and cable coating. U.S. Pat. No. 8,192,813 issued Jun. 5, 2012 to Runyan et al., assigned to ExxonMobil Chemical Patents, Inc. and Zurn Pex, Inc. teaches modifiers which may be added to polyethylene to improve the properties of cross linked polyethylene. The present invention does not contemplate the use of additives to enhance the crosslinking, particularly in view of the fact that many living hinges are used in food dispensing containers. Interestingly the 813 patent does not teach or suggest using the crosslinked polyethylene in snap tops or living hinges.

The present invention seeks to provide a durable electron beam cross linked polyethylene web suitable for use in a hinge for containers.

DISCLOSURE OF THE INVENTION

In its broadest embodiment the present invention provides one or more electron beam radiation (irradiation) crosslinked compression or injection molded polyethylene flexible hinges, comprising one or more webs having a thickness from 0.1 to 1 mm. preferably 0.2 to 0.5 mm, joining a cap comprising a rim, optionally a planar deck having at least one opening there through and a cooperating planar closing member attached to the cap by one or more of said flexible hinges wherein the number of opening and closing cycles to break at a radial bend of 90°±20° at a temperature of 25° C. of the flexible hinge is increased by not less than 30%, relative to the number of opening and closing cycles to break at a radial bend of 90°±20° at a temperature of 25° C. of a flexible hinge of the same polyethylene and the same design which has not been irridation crosslinked.

In a further embodiment said one or more webs have an increase in the number of opening and closing cycles to break at a radial bend of 90°±20° at a temperature of 25° C. of not less than 100%, relative to the number of opening and closing cycles to break at a radial bend of 90°±20° at a temperature of 25° C. of a flexible hinge of the same polyethylene and the same design which has not been irridation crosslinked.

In a further embodiment the number of opening and closing cycles to break at a radial bend of 90°±20° at a temperature of 25° C. is not less than 280 cycles, preferably greater than 400, most preferably greater than 800 cycles.

In a further embodiment said one or more webs have been irradiated with at least from 20 to 140 kGy (2-14 Mrads (MR)) preferably from 30 to 100 kGy (3 to 10 MR) of electron beam radiation.

In a further embodiment the web is a single web, the cap comprises a planar deck continuously attached to said rim, and the web connects the deck to the planar closing member.

In a further embodiment the cap is a parallelogram.

In a further embodiment the cap is circular.

In a further embodiment the planar closing member further comprises a downwardly extending continuous rim.

In a further embodiment two webs connect the rim of the planar closing member to the rim of the cap.

In a further embodiment the outer edges of said two webs subtend an angle from the center of the planar deck of from 20 to 75°.

In a further embodiment the outer edges of said two webs subtend an angle from the center of the planar deck of from 50 to 75°.

In a further embodiment the passage through the planar deck comprises an upwardly extending spout.

In a further embodiment the planar closing member comprises a downwardly extending plug on its lower surface which cooperates with said spout to seal it.

In a further embodiment on opening the planar closing member pivots on said webs through a region of higher tension to "snap" the lid open and hold it open.

In a further embodiment on closing the planar closing member pivots on said webs through a region of higher tension to "snap" the lid closed and hold it closed.

In a further embodiment there are provided additional elements on the rim of the cap to engage the rim of the planar closing member when it is shut.

In a further embodiment the polyethylene comprises one or more ethylene polymers comprising from 100 wt. % to 80 ethylene and from 0 to 20 wt. % of one or more $C_{4-8}$ alpha olefin monomers said polyethylene have a density from 0.920 g/cc to 0.970 g/cc typically not less 0.94 g/cc.

In a further embodiment the uncrosslinked polyethylene has a melt index (MI) (ASTM D 1238-2.16 kg and 190° C.) from 5 to 80, typically from 5 to 55 g/10 min.

In a further embodiment the flexible hinges are injection molded.

In a further embodiment said polyethylene has a melt index (MI) (ASTM D 1238-2.16 kg and 190° C.) from 0.25 to 50, typically from 0.5 to 30.

In a further embodiment the flexible hinges are compression molded

In a further embodiment the present invention provides the above hinge wherein the polyethylene is selected from the group consisting of high pressure polyethylene, Ziegler Natter catalyzed polyethylene, chromium catalyst polyethylene, and single site catalyzed polyethylene.

In a further embodiment the present invention provides a device for determining the flexing life of a thinned or creased region in a molded polyethylene part comprising in cooperating arrangement:

a) a plate comprising a trailing edge, two parallel sides, and a body having a rounded leading edge said body containing one or more means for fixing said part to the body which allow the polyethylene part to be fixed to the body so that the thinned region or crease of the polyethylene part is aligned with the rounded leading edge, a top bar mounted, typically on a frame having two parallel legs, between rotatable plates adjacent the rounded leading edge to hold the thinned region of the thinned part in close contact with the rounded edge;

b) two rotatable discs in cooperating parallel arrangement attached to each side of the plate proximate the rounded edge, connected to each other through a central bar beneath and proximate to said rounded edge at center holes in their foci about which the discs rotate;

c) two parallel contact bars attached at each end through holes spaced within 2 to 10 mm of the perimeter of each disc said contact bars being rotabale above and below said rounded edge so as to engage the part in a fashion that allows bending of the thinned region or crease about said rounded edge during rotation;

d) a pair of cylinders attached legs at opposite sides of plate and also connected through holes offset by from 1 to 5 cm from the respective center hole to each discs;

e) a pair of cam pins that protrude from the exterior face of each disc respectively, located in a position that is on the same radius but angularly offset relative to each other;

f) a pair of sequencing valves on each on leg;

g) a direction valve controlling the flow of fluid to the pneumatic cylinders which reverses the flow of fluid to the pneumatic cylinders when a trigger switch is contacted with a trigger pin; and h) a counter to count the number of bending cycles the part has completed.

In a further embodiment the present invention provides a squeezable container having a cap as above.

BEST MODE FOR CARRYING OUT THE INVENTION

Figure 1:
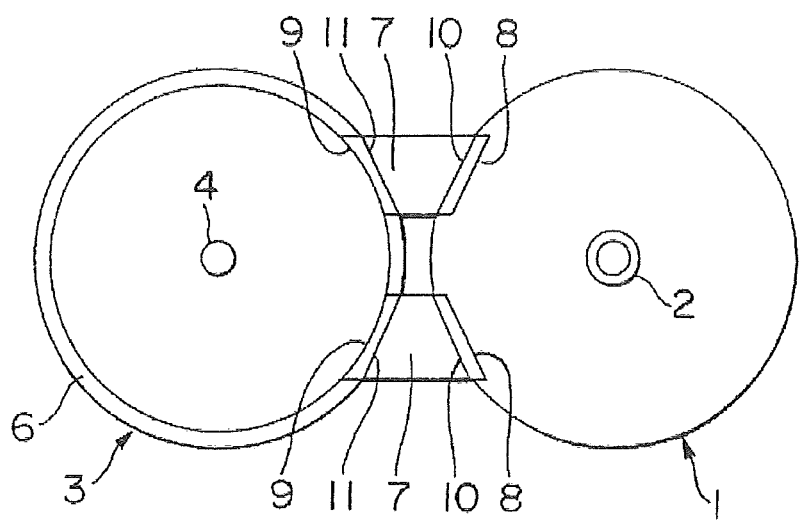
FIG. 1 is a top plan view for showing a lid closing member of the first preferred embodiment.

Other than in the operating examples or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that can vary depending upon the properties that the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

The hinges of the present invention may be used on caps for containers to dispense products such as condiments including: mustard, relish, salad dressing, honey, corn syrup, barbeque sauce, yogurt, and the like; soap; shampoo; oils; cleaners; capsules (drugs); dry spices and the like. In some instances the content flows under pressure such as a liquid, dispersion, paste or gel and the container is a squeezable container (e.g. bottle or tube) of an olefin polymer. If the hinges are used on caps to be used with foods care must be taken to only use additives approved for contact with foods (e.g. FDA). Most people have used various types of these types of hinges.

In the prior art the hinges are polypropylene as it is capable of withstanding not less than about 1000 cycles of opening and closing before breaking. However, this likely an over engineered hinge as the contents of the container are typically consumed after about a cycle of 200 openings and closings. Webs or hinges of uncrosslinked polyethylenes generally cannot meet this requirement.

The hinges of the present invention comprise one or more electron beam radiation crosslinked webs or strips of thin polyethylene joining a closing member to a cap. There are two fundamental locations for the hinge to attach a closure to. The closing member may be attached to the rim with an optional cap deck also attached to the rim, typically continuously attached, having an opening, generally in the form of an annular spout. The closing member typically has a plug or spud that cooperates to seal the spout. Alternatively, the hinge could be attached to the cap deck typically along a diameter or close to a diameter and the opening in the deck is typically a large mouthed opening. In this embodiment the closing member fits within the opening. An example of this design is the spice container design in which the lid is rectangular and the hinge runs between two parallel sides of the lid.

In some embodiments the cap only comprises a rim a hinge and a planar deck (e.g. an attached lid) such as that disclosed in WO 2010/101915 A2 published Sep. 10, 2010 (corresponds to published United States patent application 2010/0224646 A1).

In some embodiments the cap has a design comparable to that taught in U.S. patent application 2004/0118846, to Merolla assigned to Unilever now abandoned. FIG. 1 of the published application shows a large mouthed lid in which the web joins the planar closing member to the planar deck (paragraph [0040]) preferably adjacent an edge to the opening or mouth.

The hinge may also be used in snap tops. Rather than a link and pin arrangement when the upper cap pivots past a specified point the hinge passes through a high tension zone where the hinges are under maximum stress (elongation) then the hinge "snaps" into the open position with the hinge forming an inverted "V" in a lower stress position. On closing the cap passes back through a high stress (elongation) region and then the hinges snaps back to a lower stress position typically flat and resting in groves in the rim attached to the cap.

In the following description directional words such as "upwardly" and "downwardly" are employed by way of description and not limitation with respect to the upright orientation of the closure and package and directional words such as "axially" and "radially" are employed by way of description and not limitation with respect to the central axis of container or closure skirt (rim) as applicable.

Figure 2:
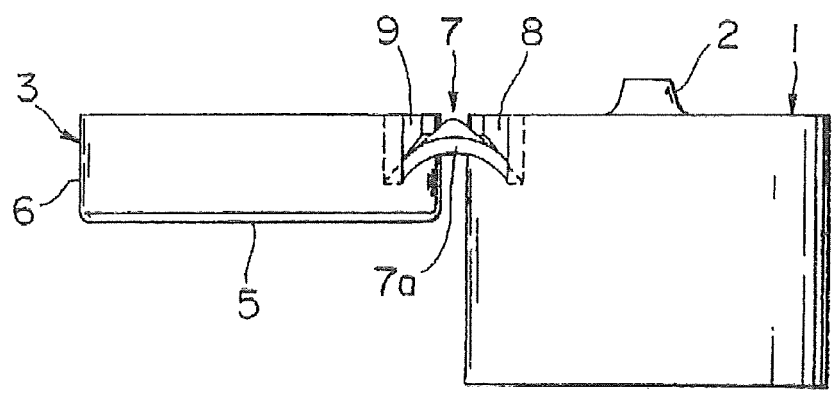
FIG. 2 is a side elevation view of FIG. 1.

A fundamental embodiment of the invention shown in FIGS. 1 and 2 of expired U.S. Pat. No. 5,148,912 issued Sep. 22, 1992 to Nozawa assigned to Yoshino Kogyosho Co., Ltd., Tokyo Japan.

The entire cap is made of polyethylene. The cap or only the hinge portions thereof are exposed to electron beam radiation after formation. The cap 1 has a downward extending circular side wall or rim which cooperates with the mouth of the dispensable container. The cap 1 has a deck or horizontal wall having a spout 2 in the central region of the cap. The lid or closing member 3 has a plug 4 mounded on the underside of the closing member (cover, deck, or top plate) 5 of the cap so that it sealingly engages (closes) spout 2. The lid or closing member 3 has a side wall 6 having a depth greater than the height of the spout 2. The hinges 7 are strips of polyethylene having a thickness from 0.1 to 1, preferably from 0.2 to 0.5 mm which have been subjected to electron beam radiation cross-linking. The hinges 7 are trapezoidal in shape having parallel side walls and inwardly slanted end walls. The end walls attach to the cap 1 and lid 3 in grooves 8 and 9 at pairs of anchor points 10 and 11. The groove is shaped so that the bottom edge that slants inwardly and upwardly. The internal edge of the hinge 7 is shorter than the external edge. As a result there is a stress or tension on the hinge 7 as is opened and there is a pivot point where the stress on the hinge as it opens is released as the hinge snaps open into a lower stress position in which the outer surface of the hinge forms a truncated inverted "V".

Typically the outer edges of the hinges 7 at the pair of anchor points 10 subtend an angle from the center of the planar deck from 20 to 75°, preferably from 50 to 75°, most preferably from 60° to 75°.

A more recent design of a cap in which the hinges of the present invention are suitable is shown in the figures of U.S. Pat. No. 6,766,926 issued Jul. 27, 2004 to Elchert assigned to Owens-Illinois Closure Inc. the text of which is herein incorporated by reference. The design contains additional elements such as a lip on the rim, a sealing edge projecting up from the cap deck and various additional latching means, for example internal ridges in the lip or elsewhere.

In other embodiments of the invention there may be a thin flexible wall of polyethylene between the hinges as taught for example by U.S. Pat. No. 4,638,916 issued Jan. 27, 1987 to Beck et al., assigned to Owens-Illinois, Inc. the text of which is hereby incorporated by reference. This provides a simpler construction. Additionally, when such a wall is radiation crosslinked its toughness also improves.

The polyethylene useful in the present invention may be any polyethylene or polyethylene blend suitable for injection or compression molding.

The polyethylene may be selected from the group consisting of high pressure polyethylene, Ziegler Natter catalyzed polyethylene, chromium catalyst polyethylene, single site catalyzed polyethylene and blends thereof.

The one or more polyethylenes comprise from 100 wt. % to 80 wt. % ethylene and from 0 to 20 wt. % of one or more $C_{4-8}$ alpha olefin monomers said one or more polyethylenes have a density from having a density from 0.920 g/cc to 0.970 g/cc typically not less 0.94 g/cc. In some embodiments the polyethylene or polyethylene blend will comprise from about 90 to 99 weight %, preferably from 95 to 98.5 weight % of ethylene and from 10 to 1, preferably from 5 to 1.5 weight % of one or more $C_{4-8}$ alpha olefins. Suitable alpha olefins include 1-butene, 1-hexene and 1-octene.

Depending on the method used for forming the lid, the uncrosslinked polyethylene may have a melt index (MI) (ASTM D 1238-2.16 kg and 190° C.) from about 0.5 to 80 g/10 min.

The uncrosslinked polyethylene or polyethylene blend may have a have a melt index (MI) (ASTM D 1238-2.16 kg and 190° C.) from 5 to 80, typically from 5 to 55 g/10 min. These resins are suitable for injection molding of the hinge and the cap.

In injection molding the polyethylene or polyethylene blend is typically fed to an extruder. The polyethylene enters a feed chamber where it is mixed by augers or screws and heated to its melting temperature. Then it is fed to a screw that pumps the molten polymer down the barrel of the extruder and into sprues (runs or channels) into molds for the part. The molds cool and the parts are released from the mold. The melt index is important for injection molding as low melt index material are more difficult to pump and or inject into the mold and this requires more energy (pressure) and time to fill the molds. In some instances it is desirable to more rapidly cool the mold in the region of the hinge to keep the polyethylene in the amorphous state.

The uncrosslinked polyethylene or polyethylene blend may have a melt index (MI) (ASTM D 1238-2.16 kg and 190° C.) from 0.25 to 50, typically from 0.5 to 30 g/10 min. These resins are suitable for compression molding of the hinge and the cap. In compression molding a charge of dry resin is fed to the mold in a partially closed state. The mold is heated to the sintering temperature of the resin around 120° C. The mold is then pressed shut under high pressure and the polyethylene sinters together to form the part. The mold is cooled, opened and the parts are ejected.

As some of the closures of the present invention are used in combination with dispensers for food the polymer or polymer blend should have a low hexane extractables less than 0.7 wt. %, preferably less than 0.6 wt. %, most preferably less than 0.55 wt. % as determined according to ASTM D5227.

The polyethylene may be made using one or more conventional platforms such as gas phase, solution and slurry polymerization. The catalyst may be one or more conventional catalysts including single site catalysts, Ziegler-Natta catalysts and chrome based catalysts (e.g. silylchromate or chromium oxide catalysts). Single site catalysts are well known in the art and include metallocenes, constrained geometry catalyst and bulky hetero ligand catalyst for example catalyst containing a phosphinimine ligand. The polyethylene or blend may be made in one reactor or in one or more reactors in series or in parallel.

The comonomer content in the polymer or polymer blend can be determined by $^{13}$C NMR, or Fourier Transform Infrared spectroscopy (FTIR) alone or in combination with gel permeation chromatography (GPC-FTIR) methods. The comonomer content of an in reactor(s) blend of polyethylenes can be determined by mathematical deconvolution methods applied to a bimodal polyethylene composition.

The short chain branching in the polyethylene is the branching due to the presence of alpha-olefin comonomer in the ethylene copolymer and will for example have two carbon atoms for a 1-butene comonomer, four carbon atoms for a 1-hexene comonomer, or six carbon atoms for a 1-octene comonomer, etc. The number of short chain branches in a polyethylene copolymer can be measured by $^{13}$C NMR, or FTIR or GPC-FTIR methods. Alternatively, the number of short chain branches in the second ethylene copolymer of an in reactor blend can be determined by mathematical deconvolution methods applied to one or more of $^{13}$C NMR, or FTIR or GPC-FTIR for a bimodal polyethylene composition.

The polyethylene or blend may have a fairly broad molecular weight distribution (Mw/Mn) from about 4 to 15, preferably less than about 10.

The polyethylene or blend may be bi or trimodal as determined by gel permeation chromatography (GPC).

In a further embodiment the polymer may comprise a blend comprising:

(1) 30 to 60 wt % of a first ethylene copolymer having a melt index, I2, of less than 4.0 g/10 min; a molecular weight distribution, $M_w/M_n$, of less than 3; and a density of from 0.925 to 0.950 g/cm$^3$; and (2) 70 to 40 wt % of a second ethylene copolymer having a melt index I2, of from 10 to 100 g/10 min; a molecular weight distribution, $M_w/M_n$, of 3 to 8; and a density higher than the density of said first ethylene copolymer, but less than 0.966 g/cm$^3$. Preferably the density of said second ethylene copolymer is less than 0.037 g/cm$^3$ higher than the density of said first ethylene copolymer; the ratio (SCB1/SCB2) of the number of short chain branches per thousand carbon atoms in said first ethylene copolymer (SCB1) to the number of short chain branches per thousand carbon atoms in said second ethylene copolymer (SCB2) is greater than 0.5.

In a further embodiment the blend has a molecular weight distribution, $M_w/M_n$, of from 4.0 to 10.0; a density of from 0.910 to 0.970 g/cc, preferably from 0.940 to 0.957 g/cm$^3$; a melt index I2, of from 0.4 to 5.0 g/10 min; a comonomer content of less than 0.75 mol % as determined by $^{13}$C NMR; an $M_z$ of less than 400,000. Preferably the polymer or polymer blend prior to irradiation has and an ESCR Condition B (10% IGEPAL) of at least 8, preferably 10, most preferably 15 hours and on crosslinking the ESCR Condition B (10% IGEPAL) should be not less than about 20 hours, preferably greater than about 35 hours.

The caps of the present invention may be prepared by compression or injection molding, preferably injection molding. The charge of polymer is fed to an extruder, in which it is melted and metered into one or a group of molds and cooled and set to the required part. Such techniques are well known to those skilled in the art. For compression molding the polymer is metered and fed to compression molds where the polymer is compressed and heated to fuse into a solid part.

The hinge in the resulting cap is then subject to radiation to cause the hinge to cross link. In practice it is often simpler to subject the entire cap to radiation to crosslink the entire cap. Devices to subject plastic parts to radiation are well known in the art. The crosslinking may be done on the site where the caps are manufactured or the caps may be tolled to a third party for cross linking. Typically the radiation will be high energy electron beam radiation, but other sources such as x-rays and possibly radio isotope radiation.

Typically the cap will be subject to a dose of radiation from about 20 to 140 KGy (K Gray) (2-14 Mrads), preferably from 30 to 100 KGy (3-10 Mrads).

After radiation the hinge should be capable of standing at least 280, preferably more than 400, most preferably more than 800, desirably at least 1000 opening and closing cycles before failure. This type of testing has been done manually in the past. The Applicants developed a machine to test the caps or simulations of the hinge (e.g. a bar having a thickness from 5 to 7 thousands of an inch (0.125 mm to 0.175 mm).

It is important to note that radiation causes crosslinking of the polyethylene which may ultimately lead to brittleness of the polymer. Accordingly care needs to be taken to avoid excess crosslinking indicated by gel formation. Typically the gel levels in the irriadiated polyethylene should not exceed about 35%, preferably less than about 15%. At higher levels of gel the hinge becomes brittle and snaps sooner.

The present invention will be illustrated by the following example.

A series of test bars having a thickness from 5 to 7 mm were injection molded from a number of polyethylene resins.

A number of the test bars were subjected to 0, 6, 10, 14 and 18 MR of electron beam radiation.

Figure 3:
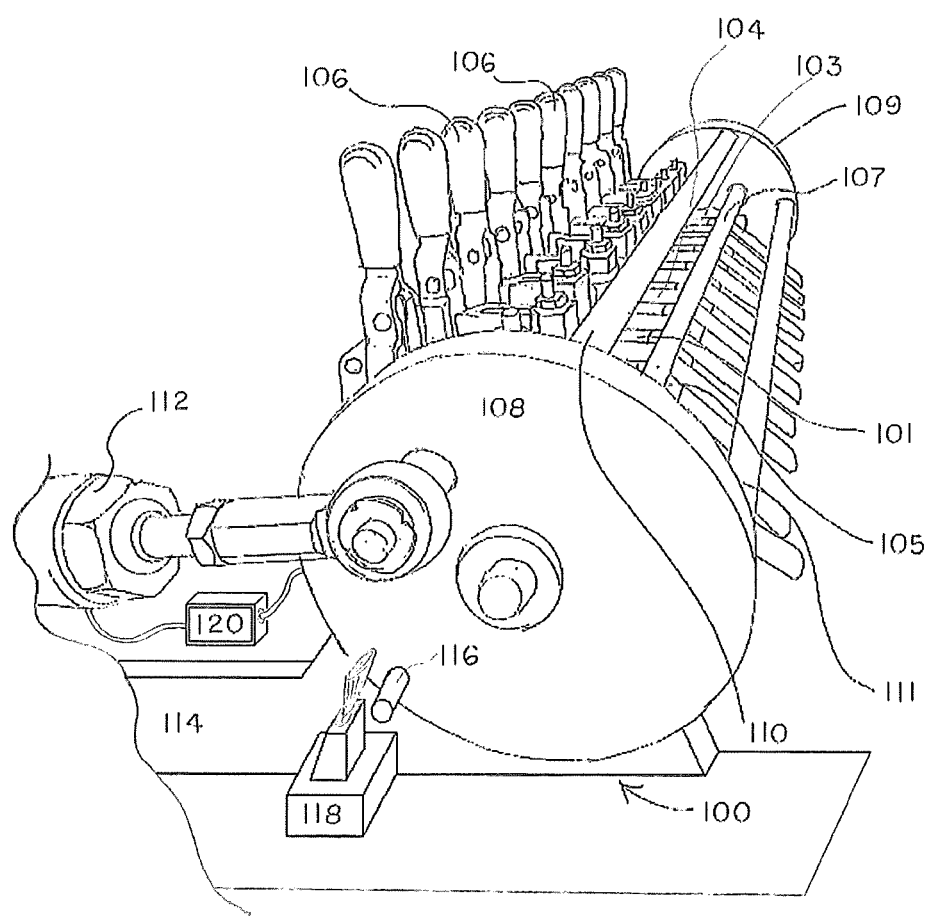
FIG. 3 is a drawing of the automated tester used in the examples.

Then irradiated and un-irradiated test bars were tested for bending cycles at a radius of 90°±20° in the automated hinge tester of FIG. 3.

FIG. 3 is a drawing of a device (100) for determining the flexing life of a cap or a thinned or creased region in a molded polyethylene part comprising in cooperating arrangement:

a) a plate (101) comprising a trailing edge (102 not shown), two parallel sides (103) a body (104) having a rounded leading edge (105) said body containing one or more means for fixing said part to the body (106) typically, comprising a series of evenly spaced threaded holes or clamps which allow the polyethylene part to be fixed to the body (104) so that the thinned region or crease of the polyethylene part is aligned with the rounded leading edge (105) a top bar 107 mounded between rotatable disc adjacent the rounded leading edge 105 to hold the thinned region of the thinned part in close contact with the rounded edge 105.

b) two rotatable discs (108 and 109) in cooperating parallel arrangement attached to each side of the plate proximate the rounded edge connected to each other through a central bar (not shown) beneath and proximate to said rounded edge (105) at center holes (not shown) in their foci about which the discs rotate;

c) two 2 parallel contact bars (110 and 110) attached at each end through holes spaced within 2 to 10 mm of the perimeter of each disc (108 and 109) said contact bars being rotatable above and below said rounded edge (105) so as to engage the test object in a fashion that allows bending of the thinned region or crease about said rounded edge (105) during rotation;

d) a pair of pneumatic cylinders (112 and 113 (not shown)) although other types of cylinders (liquid driven) or drive means such as an electric motor could be used attached to legs (114 and 115 (not shown)) at opposite sides of plate (101) and also connected through holes offset by from 1 to 5 cm from the respective center hole to each disc (108 and 109);

e) a pair of cam pins (116 (and 117 not shown)) that protrude from the exterior face of each disc (108 and 109) respectively, located in a position that is on the same radius but angularly offset relative to each other;

f) a pair of sequencing valves (118 (and 119 not shown)) one each on legs 114 and 115 respectively;

g) a direction valve (120) controlling the flow of air to the pneumatic cylinders which reverses the flow of air to the pneumatic cylinders when a sequencing valve (one of 118 or 119) is contacted with a cam pin (one of 116 and 117); and h) a counter (121 (not shown) to count the number of bending cycles the part has completed that typically cooperates with one of the cam pins (116 or 117).

In operation the angular offset between the two cam pins controls the degree of rotation of the pivoting discs. The sample is mounted on the plate so that the thinned section is at or proximate the rounded edged. The portion of the sample which extends beyond the rounded edge fits between the parallel contact bars. Air is provided to the pneumatic cylinders and the rotating discs rotate until a cam pin strikes a sequencing valve which reverses the flow of air to the pneumatic cylinders causing the discs to rotate in the opposite direction until the cam pin on the other disc strikes the sequencing valve on the other leg to cause the air flow to the cylinders to be reversed causing the disc to rotate in the opposite direction. This cycle repeats itself until the part breaks. A counter keeps track of the number of cycles until the part breaks. A technician observes the samples and turns the machine off when a part breaks and records the number of cycles.

A series of 10 samples of the same polymer for each irradiation level are tested at the same time and the number of cycles for each bar to break is recorded together with the range of cycles for all of the samples to break.

The control is 0 irradiation is the control for each sample.

The data is set forth in table 1 below together with the density, and MI of the resin or blend tested.

TABLE 1

| Sample | Radiation Treatment (MR) | Average Cycles to Failure | Minimum Cycles to Failure | Maximum Cycles to Failure |
|---|---|---|---|---|
| SCLAIR® 2714 | 0 | 658 | 285 | 1592 |
| | 6 | 1740 | 760 | 3156 |
| | 10 | 13066 | 2205 | 26500 |
| | 14 | 3026 | 1450 | 4420 |
| | 18 | 4128 | 970 | 5980 |
| SCLAIR® IG454-A | 0 | 5576 | 3990 | 8023 |
| | 6 | 12100 | 7630 | 19081 |
| | 10 | 18445 | 8377 | 27615 |
| | 14 | 30198 | 6673 | 74186 |
| | 18 | 7219 | 3931 | 13339 |

Figure 4:
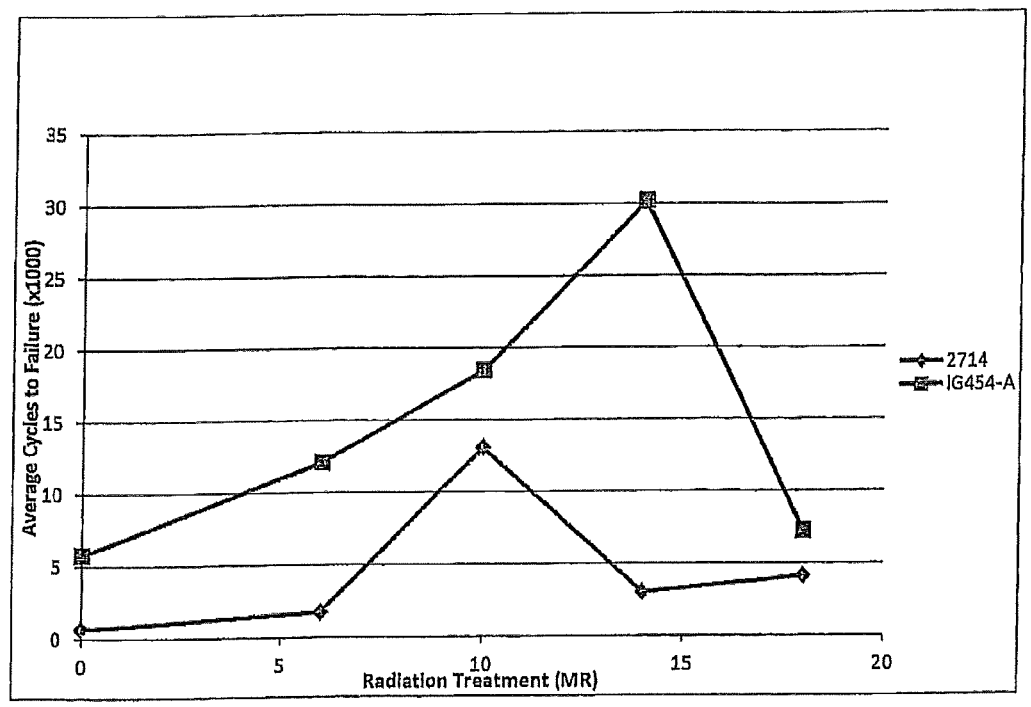
FIG. 4 is a plot of average cycle to failure as a function of radiation treatment for the examples.

A plot of average cycle failure as a function of radiation treatment is set out in FIG. 4.

Additionally, the samples were analyzed for gel levels.

For SCLAIR® 2714 an average life cycle of about 10,000 resulted from a product having about 25% gel and at 35% gel the product appears to have gone brittle. For SCLAIR® IG454-A, an average life cycle of about 10000 was observed at a gel level of 15% and an average life cycle of 30000 was observed at a gel level of about 35%. At 50% gel the product appeared to become brittle.

As the test was on a simple thinned bar area the data shows relative improvement in the bar. The data is indicative of a cap but the bar does not have the internal stress of a snap lid so the data may be higher than for a snap top lid. Some of the irradiated bar samples were capable of withstanding a life cycle of more than 8000 opening and closing cycles.

INDUSTRIAL APPLICABILITY

The caps prepared in accordance with the present invention may be used in a number of applications where "snap top" lids are generally used, in condiment containers such as oils, salad dressings, ketchup, mustard and relish containers.

The invention claimed is:

1. A cap comprising a rim, a deck having an opening therethrough, and a cooperating lid attached to the rim by a hinge comprising one or more webs of injection or compression molded polyethylene wherein the polyethylene is chosen from high pressure polyethylene, Ziegler Natter catalyzed polyethylene, chromium catalyst polyethylene, single site catalyzed polyethylene, and mixtures thereof, each of said one or more webs having a thickness from 0.1 to 1 mm and having been radiation crosslinked and having a gel level not exceeding 35 wt. %; wherein the number of opening and closing cycles to break at a radial bend of 90°±20° at a temperature of 25° C. of the hinge is increased by not less than 30%, relative to the number of opening and closing cycles to break at a radial bend of 90°±20° at a temperature of 25° C. of a hinge of the same polyethylene and the same design which has not been irradiation crosslinked.

2. The cap according to claim 1, wherein the hinge has an increase in the number of opening and closing cycles to break at a radial bend of 90°±20° at a temperature of 25° C. of not less than 100%, relative to the number of opening and closing cycles to break at a radial bend of 90°±20° at a temperature of 25° C. of a hinge of the same polyethylene and the same design which has not been irradiation crosslinked.

3. The cap according to claim 2, wherein the hinge has a number of opening and closing cycles to break at a radial bend of 90°±20° at a temperature of 25° C. that is not less than 280 cycles.

4. The cap according to claim 3, wherein said one or more webs have been irradiated with from 20 to 140 kGy (6-14 Mrads (MR)) of electron beam radiation.

5. The cap according to claim 3, wherein the hinge comprises a single web.

6. The cap according to claim 5, in the shape of parallelogram.

7. The cap according to claim 5, which is circular.

8. The cap according to claim 5, wherein the lid further comprises a downwardly extending continuous rim.

9. The cap according to claim 8, wherein the hinge comprises two webs.

10. The cap according to claim 9, wherein the outer edges of said two webs subtend an angle from the center of the deck of from 20 to 75°.

11. The cap according to claim 10, wherein the outer edges of said two webs subtend an angle from the center of the deck of from 50 to 75°.

12. The cap according to claim 5, wherein the opening through the deck comprises an upwardly extending spout.

13. The cap according to claim 12, wherein the lid comprises a downwardly extending plug on its lower surface which cooperates with said spout to form a seal on closing closed.

14. The cap according to claim 5, wherein on opening, the lid pivots on said web through a region of higher tension to "snap" the lid open and hold the lid so the cap is in an open position.

15. The cap according to claim 14, wherein on closing, the lid pivots on said web through a region of higher tension to "snap" the lid closed and hold the lid so the cap is in a closed position.

16. The cap according to claim 15, wherein there are provided additional elements on the rim of the cap that engage the rim of the lid when the cap is in a closed position.

17. The cap according to claim 1, wherein the polyethylene has a density from 0.920 g/cc to 0.970 g/cc and the polyethylene comprises one or more ethylene polymers comprising from 100 wt. % to 80 ethylene and from 0 to 20 wt. % of one or more $C_{4-8}$ alpha olefin monomers.

18. The cap according to claim 17, wherein the polyethylene, prior to being radiation crosslinked, has a melt index (MI) (ASTM D 1238-2.16 kg and 190° C.) from 5 to 80 g/10 min.

19. The cap according to claim 18, wherein the hinge is injection molded.

20. The cap according to claim 17, wherein the polyethylene, prior to being radiation crosslinked, has a melt index (MI) (ASTM D 1238-2.16 kg and 190° C.) from 0.25 to 50 g/10 min.

21. The cap according to claim 20, wherein the hinge is compression molded.

22. The cap according to claim 1 in cooperating arrangement with a squeezable container.

* * * * *